United States Patent [19]

Rothenberg

[11] Patent Number: 4,786,601
[45] Date of Patent: Nov. 22, 1988

[54] TISSUE CULTURE HOLDER

[76] Inventor: Barry E. Rothenberg, 149 12th St., Del Mar, Calif. 92014

[21] Appl. No.: 58,046

[22] Filed: Jun. 4, 1987

Related U.S. Application Data

[63] Continuation-in-part of Ser. No. 712,413, Mar. 15, 1985, Pat. No. 4,673,651.

[51] Int. Cl.$^4$ .............................................. F23D 3/34
[52] U.S. Cl. ...................................... 435/301; 435/284
[58] Field of Search ..................... 435/284, 297–301; 220/21, 23.2, 23.8, 420, 422, 427, 428, 426; 34/192, 195, 197, 199, 237, 238; 261/DIG. 3, 125; 422/102; 436/809

[56] References Cited

U.S. PATENT DOCUMENTS

| | | | |
|---|---|---|---|
| 2,240,602 | 5/1941 | Bartsch | 220/427 |
| 2,725,733 | 12/1955 | Davis | 220/420 |
| 2,771,754 | 11/1956 | Winkler | 220/427 |
| 3,107,204 | 10/1963 | Brown et al. | 195/103.5 |
| 3,776,818 | 12/1973 | Khan | 195/139 |
| 3,805,018 | 4/1974 | Luong et al. | 220/427 |
| 3,969,496 | 7/1976 | Schrot | 424/1 |
| 3,997,404 | 12/1976 | Waters | 435/300 |
| 4,030,980 | 6/1977 | Beckford et al. | 195/139 |
| 4,572,402 | 2/1986 | Gervais et al. | 220/420 |
| 4,657,867 | 4/1987 | Guhl et al. | 435/301 |

Primary Examiner—Samuel Scott
Assistant Examiner—Noah Kamen
Attorney, Agent, or Firm—Brown, Martin, Haller & Meador

[57] ABSTRACT

A tissue culture holder has an insulating chamber in its base below the culture containing chamber or chambers. The insulating chamber is filled with air or a clear liquid and may be sealed in a low humidity environment so that, in the case of an air-filled chamber, there will be minimal or no condensation in the chamber. In the case of a multi-well tray, the insulating chamber below the wells may be sealed or may have passageways for circulating air through the chamber and up into the space above the wells.

12 Claims, 1 Drawing Sheet

TISSUE CULTURE HOLDER

CROSS REFERENCE RELATED TO THE APPLICATION

This application is a continuation-in-part of my Application Ser. No. 712,413, entitled "Multi Cell Tray", which was filed on Mar. 15, 1985, now U.S. Pat. No. 4,673,651.

BACKGROUND OF THE INVENTION

The present invention relates generally to tissue culture holders such as dishes, flasks, and multi well trays which have one or more chambers or wells for holding tissue cultures or other reagents for testing.

Tissue culture holders of this type generally rest directly on metal grill shelves in incubators, so that when the incubator door is opened and cool air rushes in and through the shelf openings, uneven heating and cooling effects will result in the culture or reagents under test. It has been shown that this results in uneven heating effects which are aligned with the grill pattern of the shelf on which the disk or tray stands. It is difficult to overcome these problems since any insulation would interfere with the clear viewing of the culture or cultures in the wells, which normally have transparent walls to allow the cultures under test to be viewed through the bottom of the culture holder using an inverted microscope.

SUMMARY OF THE INVENTION

It is an object of the present invention to provide a culture holder in which the effects of uneven heating are reduced or minimized.

According to the present invention a culture holder is provided which has at least one culture chamber for containing a tissue culture or other reagent and an insulating chamber below the culture chamber for insulating the base of the culture chamber.

The culture holder may be a flask or dish for containing a single tissue culture or other reagent with a double walled base defining the insulating chamber, or it may be of the multi-well tray type. The multi-well tray consists of a base having a plurality of wells or chambers for containing cultures and a cover placed over the base to cover the base and wells. The base has a downwardly depending skirt which extends below the base of the wells, and a bottom wall defining the insulating chamber below the wells. The insulating chamber is preferably a sealed chamber and may contain air or any suitable clear fluid which will not interfere with clear viewing of the culture or cultures. This provides a thermal sink which surrounds the culture chamber or wells in the case of a multi-well tray. The fluid may be cold or warm, depending on the temperature environment desired for the particular test reagents.

In an alternative arrangement, the insulating chamber in the base of a multi well tray may be provided with passageways to permit gas to flow through the insulating chamber and into the space between the base and cover above the wells. The chamber in this case may contain a liquid both to himidify the gas and to act as a thermal sink surrounding and insulating the wells.

The height of the insulating chamber below the culture chamber or wells is critical. It must be a relatively small gap so that it will not interfere with clear viewing of the culture through the bottom of the culture holder, while at the same time providing sufficient insulation. The thickness or depth of the insulating chamber below the bottom of culture chamber or well should preferably be no greater than 5/16 inch.

BRIEF DESCRIPTION OF THE DRAWINGS

The present invention will be better understood from the following detailed description of some preferred embodiments of the invention, taken in conjunction with the accompanying drawings, in which like reference numerals refer to like parts and in which.

DESCRIPTION OF THE PREFERRED EMBODIMENTS

Figure 1:
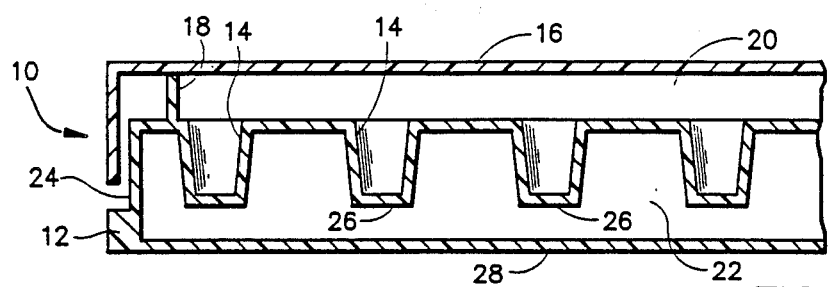
FIG. 1 is a cross-sectional view through a multi well tray according to a first embodiment of the present invention having an insulating chamber below the wells.

FIG. 1 of the drawings shows a culture holder comprising a multi well tray 10 having a base 12 containing a number of individual wells 14 into which tissue cultures or other reagents may be placed for testing, experimental and other purposes. A removable cover or lid 16 is placed over the base to cover the open upper ends of the wells 14 and is spaced above the level of the wells by suitable ribs or spacers 18, or by a raised rim having passageways for gas distribution, as described in my copending application Ser. No. 712,413 referred to above. This allows gas, for example air, to be distributed into the space 20 above the wells. The tray 10 may be of any suitable shape, such as square, circular or rectangular. The tray is made of a suitable transparent plastics material or glass to allow the contents of the wells to be viewed at all times.

In the past such culture trays have been placed directly on the metal grill shelves of incubators while under test. When the incubator door is opened to remove other culture holders or insert new ones, cool air will circulate around the incubator and through the shelf openings beneath the wells, resulting in uneven evaporation effects in the cultures under test. In the present case the culture tray 10 is provided with an insulating chamber 22 beneath the wells to reduce or avoid this problem.

As shown in FIG. 1, the base 12 has a peripheral skirt 24 which extends below the level of the bottom walls 26 of the wells, and the open lower end of the skirt is sealed by a bottom wall or panel 28 which is preferably sonically welded around its periphery to the lower edge of the skirt. This forms the lower insulating chamber 22, which may be filled with air or any other suitable fluid. The chamber 22 in this embodiment is sealed, and is preferably manufactured in a low or zero humidity environment, or in a vacuum, to avoid or reduce condensation in the chamber which could restrict viewing of the wells through the bottom of the tray.

In FIG. 1 the chamber 22 is filled with air or other gas. However, it may alternatively be filled with a suitable clear liquid. In this case the liquid could be cooled or heated to provide the desired temperature environment for a particular culture or reagent under test. The base in this case will be formed with a hole in its upper wall for filling the chamber with liquid. The hole will then be sealed to retain the liquid.

The dimensions of the insulating chamber are critical. If the chamber is too large, it will impede the viewing of the cultures during testing through the bottom wall via an inverted microscope. Thus the gap between the bottom walls of the wells and the bottom wall of the chamber must be sufficiently small so that it will not interfere with the clear viewing of the cultures in the wells through the microscope, i.e. so that the wells will still be within the focal plane of the microscope used. In the preferred embodiment, the depth of the insulating chamber below the bottom walls of the wells is no greater than 5/16 inch. This ensures clear viewing of the contents of the wells via a standard inverted microscope as used in tissue culture applications.

Figure 2:
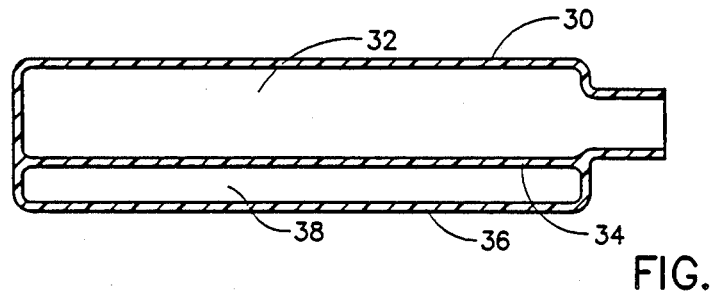
FIG. 2 is a cross-sectional view similar to FIG. 1 showing a culture flask according to a second embodiment of the invention.

Although the insulating chamber is shown in the base of a multi-well tray in the embodiment of FIG. 1, in practice such a chamber can be provided in the bottom of any culture holder, such as a culture plate or a culture flask. FIG. 2 shows a culture flask 30 of the type generally used to hold a single tissue culture or reagent in chamber 22. A double wall 34, 36 is provided on the side of the flask which normally rests on an incubator shelf, forming an insulating chamber 38 below the specimen-holding chamber 32. Again the chamber 38 is hermetically sealed and the flask is suitably manufactured in a low or zero humidity environment when chamber 38 is to be an air or gas chamber, to avoid or minimize condensation within chamber 38. The height of insulating chamber is also chosen according to the focal plane of the viewing microscope, and is preferably no greater than 5/16 inch. Chamber 38 may alternatively be filled with a suitable clear liquid which can be cooled or heated to provide temperature control.

Figure 3:
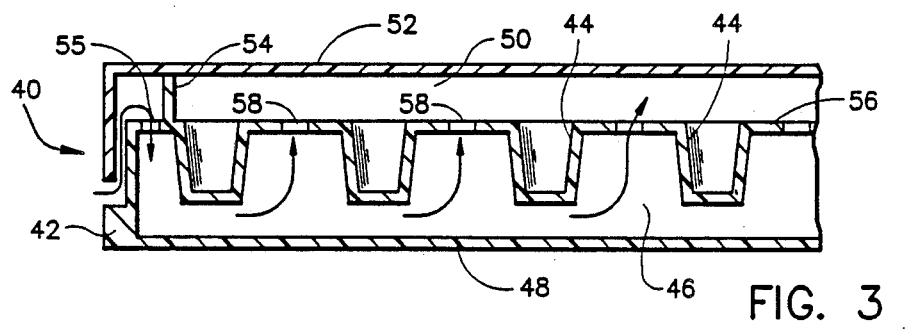
FIG. 3 is a cross-sectional view similar to FIG. 1 showing a multi-well tray according to a third embodiment of the present invention.
Figure 4:
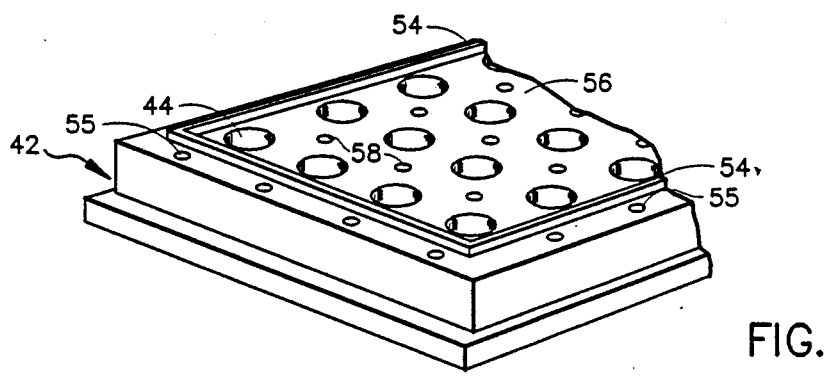
FIG. 4 is a perspective view showing the base of the tray in FIG. 3.

FIGS. 3 and 4 of the drawings show a third embodiment of the invention. In this embodiment a multi-well tray 40 has a base 42 including a plurality of wells 44, and a chamber 46 is defined below the wells by bottom wall 48 in a similar manner to the embodiment of FIG. 1. However, in this embodiment the chamber 46 is not sealed but has passageways for dispersing gas through the chamber 46 and into the space 50 above the wells between the base 42 and cover 52 of the tray.

An upstanding ridge or rim 54 extending around the well area spaces the cover above the base and forms an enclosed chamber above the wells. Alternatively, a downwardly depending ridge could be provided in the cover, or cooperating rims could be provided on the base and cover. A series of openings 55 is the upper wall 56 of the base outside the rim 54 allow air to flow in the direction of the arrow into the chamber 46. A second series of passageways or openings 58 are provided in the upper wall 56 within the well area, suitably in the gaps between wells as illustrated in FIG. 4. Gas entering the chamber 46 via openings 55 will be dispersed via openings 58 up through the base of the tray and into the space above the wells, with the openings arranged so that gas is dispersed substantially evenly to all the wells, to reduce or avoid uneven evaporation effects. At the same time, the wells will be insulated from cooling air flowing upwardly through the incubator by the chamber below the wells. The contact between the base and the cover forms a seal against ingress of substantial quantities of gas at their contacting surfaces when the cover is placed over the base, such that the major gas flow is via the chamber 46 through openings 58.

Hydrophobic filters may be provided in the openings 55 to filter the incoming gas or air to remove particles which may contaminate the cultures. The openings 55 may be replaced with slots or channels to receive a continuous filter strip or strips. The filter pore size will be no smaller than 0.45 microns for effective passage of gas.

If desired a suitable liquid such as water may be provided in the chamber 46 so that air or other gas flowing through the chamber into the space above the wells will be humidified. The water will act as a thermal sink surrounding the wells 44 when the chamber is full, thus helping to insulate the wells and produce even culture results in all the wells.

As mentioned above, the culture tray or holder in all the embodiments is preferably of a transparent material to allow the user to have a clear and continuous view of the well or holder contents during experimentation. The depth of the chamber below the bottom wall of the well or culture chamber will be relatively small to ensure that the chamber will not interfere with clear viewing of the specimen or specimens, and in all cases this height is suitably no greater than 5/16 inch.

According to another aspect of the present invention, a method of making a multi-well culture tray with an insulating chamber below the wells is provided. The lid of the tray is suitably molded from transparent plastics material in the standard manner. The base is formed by injection molding plastics material between male and female die parts to form the desired number of wells. This is again a standard technique in manufacturing multi-well trays.

In order to prevent vacuum puckering in the lower wall of each well as the two die parts are separated, a pop-release valve is provided to blow air into the gap between the parts at they are separated, preventing formation of a vacuum. This results in smoother well walls restricting uneven cell aggregation effects as a result of uneven well walls.

Once the upper wall of the base is formed, the bottom wall, which may be a flat plate or a plate with an upturned rim, is suitably attached to the lower edge of the base skirt 24. This is preferably done by sonic welding or alternative bonding techniques around the joint in a vacuum or in a low or zero humidity environment, to avoid or reduce condensation in the chamber below the wells.

Although some preferred embodiments of the invention have been described above by way of example only, it will be understood by those skilled in the field that modifications may be made to the disclosed embodiments without departing from the scope of the invention, which is defined by the appended claims.

I claim:

1. A tissue culture holder, comprising:
a relatively flat container having at least one culture chamber for containing a reagent under test a relatively flat cover for said container, and a separate insulating chamber below the culture chamber for insulating the culture chamber, the insulating chamber having a transparent bottom wall for allowing viewing of the contents of the culture chamber from beneath the holder, and the depth of the insulating chamber between the bottom wall of the culture chamber and the bottom wall of the insulating chamber being no greater than 5/16 inch.

2. The holder according to claim 1, wherein the container comprises a base having a plurality of wells within a well area for containing reagents, and spacer means for spacing the cover above the base to define a space above the wells, the insulating chamber comprising a chamber below the wells.

3. The holder according to claim 2, wherein the base comprises an upper wall in which the wells are located, a downwardly depending skirt around the periphery of the upper wall, and a bottom wall extending across the lower end of the skirt to define the insulating chamber.

4. The holder according to claim 3, wherein the insulating chamber is a sealed chamber.

5. The holder according to claim 4, wherein the insulating chamber is air filled and substantially moisture free.

6. The holder according to claim 4, wherein the insulating chamber contains a clear liquid.

7. The holder according to claim 6, wherein the liquid is water.

8. The holder according to claim 3, wherein the insulating chamber has passageways for permitting gas to flow through the insulating chamber and into the space above the wells.

9. The holder according to claim 8, wherein the passageways comprise a first set of openings in the upper wall of the base surrounding the well area for allowing gas to flow into the insulating chamber, and a second set of openings in the upper wall of the base between the wells for permitting gas to flow upwardly out of the insulating chamber and into the space above the wells.

10. The holder according to claim 8, wherein the base chamber is filled with a liquid to provide a thermal sink surrounding the wells.

11. The tissue culture holder according to claim 1, wherein the insulating chamber is gas-filled and substantially moisture free.

12. A tissue culture holder, comprising; a flask of elongate, bottle-like shape having a narrow neck portion at one end and a wider, body portion extending from the neck portion and terminating in an end wall; a dividing wall extending along the length of the body portion parallel to the central longitudinal axis of the flask up to the end wall to divide the body portion into a culture chamber for containing a reagent under test and a separate insulating chamber; the culture chamber communicating with the neck portion of the flask and the insulating chamber being sealed and having a depth of no greater than 5/16 of an inch between the dividing wall and a side wall of the flask.

* * * * *